United States Patent [19]

Torresin

[11] 4,375,169
[45] Mar. 1, 1983

[54] TURBULENCE CONVEYOR FLOW METER

[75] Inventor: Giuseppe Torresin, Padova, Italy

[73] Assignee: Francesca Succu, Padova, Italy

[21] Appl. No.: 185,683

[22] Filed: Sep. 10, 1980

[30] Foreign Application Priority Data

Sep. 14, 1979 [IT] Italy .............................. 84138 A/79

[51] Int. Cl.$^3$ .............................................. G01F 1/22
[52] U.S. Cl. ................................................ 73/861.53
[58] Field of Search ........... 73/861.42, 861.52, 861.53, 73/861.62; 128/725

[56] References Cited

U.S. PATENT DOCUMENTS

| 1,098,247 | 5/1914 | Gibbs .............................. 73/861.62 |
| 2,606,445 | 8/1952 | Eckman .......................... 73/861.53 |
| 3,817,099 | 6/1974 | Bubniak et al. ................ 73/861.53 |
| 3,960,142 | 6/1976 | Elliot et al. ..................... 128/725 |
| 4,193,301 | 3/1980 | Ferrentino ...................... 73/861.53 |

Primary Examiner—Herbert Goldstein
Attorney, Agent, or Firm—D. Paul Weaver

[57] ABSTRACT

A turbulence conveyor flow meter for medical use includes a turbulence chamber with variable input and-/or output areas, a transducer system for the pressure drop across the turbulence chamber and connected between two external points of the chamber, a servo-mechanism under control of the transducer system, acting on the flow to be measured, and a detector of the measured flow.

8 Claims, 8 Drawing Figures

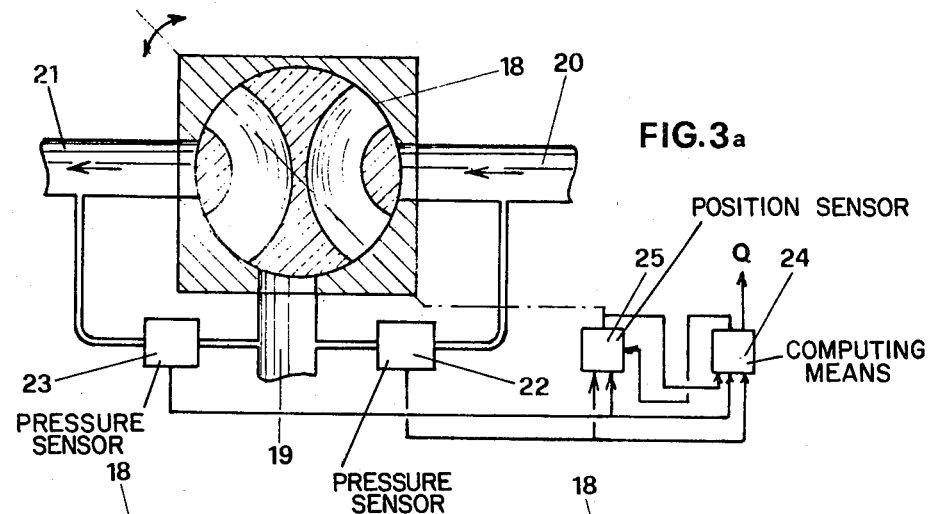
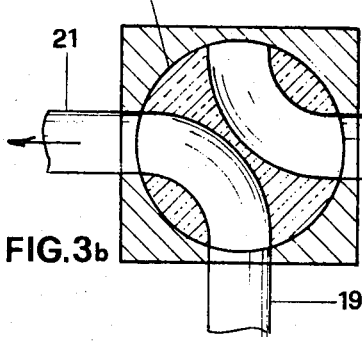
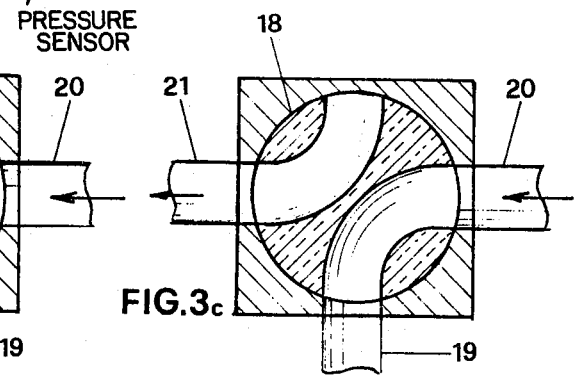
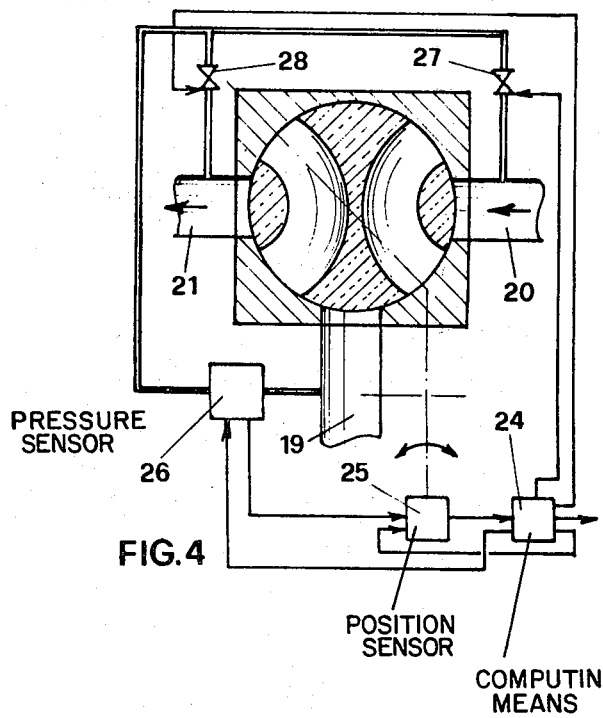
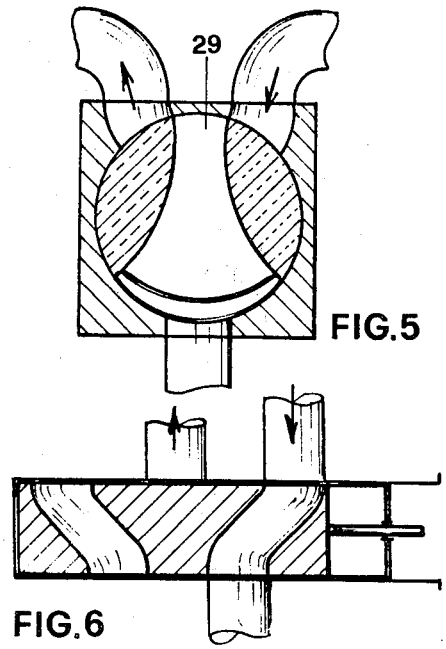

TURBULENCE CONVERYOR FLOW METER

BACKGROUND OF THE INVENTION

The present invention relates to a turbulence conveyor flow meter for medical use, particularly in physiopathology, in pulmonary and cardiocirculatory medicine and in anaesthesia.

In the medical field, particularly with reference to the pulmonary function, there exists a need for exact measurements of flows within a wide range of values, from zero to hundreds of liters per minute. To carry out such measurements, two types of devices are known in the prior art, namely, laminar and turbulence flow meters.

Among laminar flow meters, the most widely used is the Fleisch pneumotachograph. It comprises an undulated thin plate spirally wound, flowing a diaphragm or laminar, which obstructs air flow. The pressure drop at the ends of the diaphragm gives a measure of the flow. Such a device, however, collects dirt and can be obstructed when the flows are unclean. Moreover, it cannot be used for high flow values, which alter the laminar motion of the flow.

To overcome these limitations, turbulence flow meters have been introduced. They consist of obstacles to the flow which produce turbulence in the flowing fluid. The pressure drop is proportional to the flow being tested according substantially to a quadratic law.

Among turbulence flow meters, the Elliot's device is known (Journal of Applied Physiology, 1975, pages 456-460) comprising a chamber, the input and output ducts of which are misaligned. The flow value is measured by the pressure drop at the two chamber ends. An advantage of such a device is its working stability and lack of sensitivity to physiologically polluted flows. On the other hand, a limitation of the device is its excessive resistance to the flow for high values of the flow (when it is higher than 120 liters per minute) and its lack of sensitivity to low values of flow (less than 3 liters per minute). In fact, for such low values, no appreciable turbulence takes place.

Flow meters provided with a resilient membrane are also known (Franetzki, Ph.D dissertation, 1975, Universitat Friedriciana Karlsruhe). In them, the resistance to the flow is inversely proportional to the flow. These flow meters can be built with a convenient material, and shaped in such a way, so as to establish a laminar relation between the pressure drop and the flow to be measured. The sensitivity to respiratory soiling (sputum) and the levity of the membranes makes these flow meters unreliable.

All of the flow meters referred to above, both turbulence and laminar flow types, possess some drawbacks in the measurement of flows. Moreover, they are not suited to the conveyance of expired flows for various reasons. This feature, though not strictly required for some tests (spirometry) becomes essential in the rebreathing technique. As known, the aim of rebreathing techniques is the analysis and/or the intervention in the respiratory and/or cardiocirculatory function for clinical or therapeutic purposes (nitrogen wash-out, oxygen rebreathing, anaesthetics inhalation).

The problem of conveying expired flows is solved at present by combining together independent flow meters and conveyors. In order to avoid measurement disturbances, the valve (conveyor) has to be placed not too near the flow meter. This causes an undesired dead space when the flow meter is placed between patient and valve; therefore, the necessity of having more flow meters to avoid the dead space, or at least a means to measure the flow in one of its passages.

Due to these limitations, some rebreathing techniques proposed in the last century (Pfueger's School, Germany, 1870-1873) and well developed by the physiologists in the sixties (Doehring and Thews, Pfeugers Archiv. 311, 1969 pages 326-341) did not find clinical application.

The object of the present invention is to overcome the limitations and drawbacks above-referred to, by providing a reliable compact device, of simple construction and easy use, in the medical field, allowing the measurement and conveyance of respiratory flows, particularly in physiopathology, in pulmonary and cardiocirculatory medicine and in anaesthesia.

The above objective is attained in accordance with the invention with a turbulence conveyance flow meter for medical use comprising a turbulence chamber with variable input and/or output areas, a transducer system for the pressure drop across the turbulence chamber and connected between two external points of the chamber, a servomechanism under control of the transducer system, acting on the flow to be measured, and a detector of the measured flow.

According to the invention, the servomechanism may be of the type acting on the input and/or output areas.

Advantageously, the flow meter may comprise a tap or valve with an intercepting element, provided with at least a passageway forming, when it is open to the flow, a turbulence chamber. Still according to the invention, the flow meter may comprise a microprocessor controlling the servomechanism, according to the signals of the detector and to the actual input/output areas of the chamber, and detecting the measured flow.

The turbulence chamber of the flow meter may be provided with at least an input duct and an output duct, for the continuous sampling of the gas to be measured and for its compensation with an equal volume of gas.

Other objects and advantages of the invention will become apparent during the course of the following description.

BRIEF DESCRIPTION OF THE DRAWINGS

FIG. 3a is a similar sectional view of a flow meter according to the invention having a two-way tap.

FIGS. 3b and 3c are sectional views showing the two-way tap in FIG. 3a in different operational modes.

FIG. 4 is a sectional view of a flow meter according to the invention with one pressure transducer.

FIG. 5 is a sectional view showing a different embodiment of the tap.

FIG. 6 is a sectional view showing a further embodiment of the tap of the flow meter.

DETAILED DESCRIPTION

Figure 1:
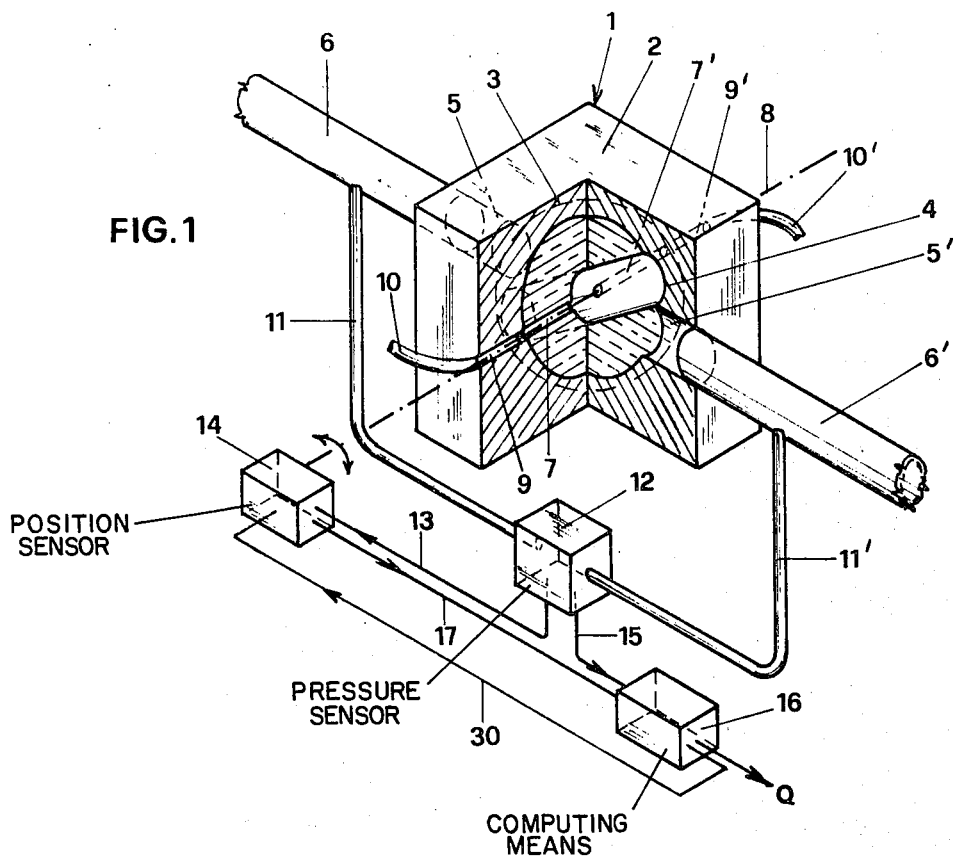
FIG. 1 is a perspective view, partly in section, of a flow meter according to the invention, including a one-way tap as an interception element.
Figure 2:
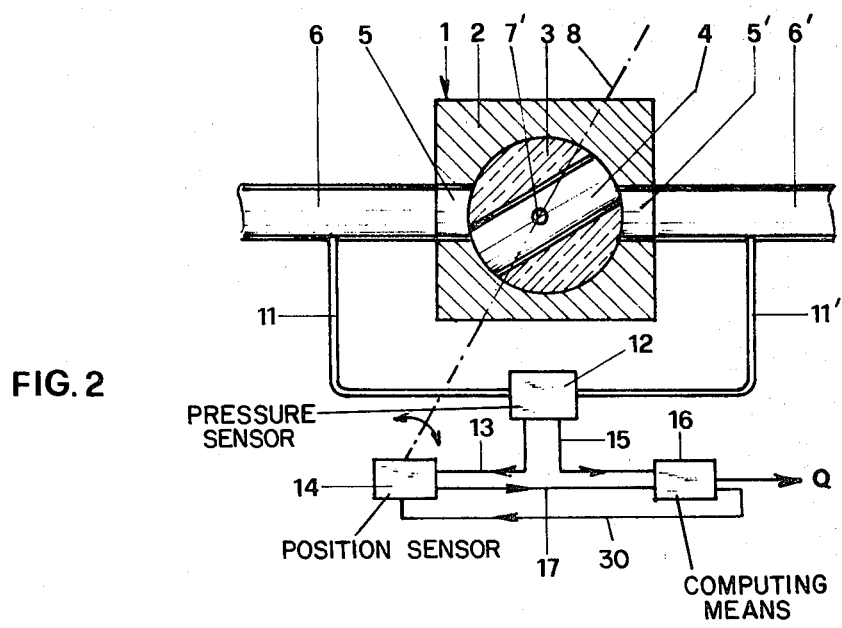
FIG. 2 is a sectional view of the flow meter in FIG. 1.

Referring in detail to FIGS. 1 and 2 wherein like numerals designate like parts, a flow meter includes a tap 1 consisting of a body 2 out of which aspherical cavity has been grooved, and a spherical intercepting element 3 arranged in said cavity. The intercepting element 3 has a diametrical duct or passage 4, which for a given position of the element 3 relative to the body 2 is axially aligned with two passageways 5, 5', formed in the body 2. The passageways 5, 5' extend beyond the body 2 into two external conduits 6, 6', whereof the conduit 6 is in contact with the patient's mouth, and the conduit 6' is open to external air. In the interception element 3, two coaxial ducts 7, 7' are formed. The axis of these coaxial ducts is othogonal to the axis duct 4 and coincides with the rotational axis of spherical element 3 with respect to the body 2. The two ducts 7, 7' extend into the body 2 of the tap in further ducts 9, 9' and then outwardly into conduits 10, 10'.

From the ducts 6, 6', start respectively conduits 11, 11', communicating with a pressure transducer 12, which transforms the difference of pressure Δp observed into electrical signals. These signals are sent through a connecting element 13 to a servomechanism 14, which controls the angular position of the intercepting element 13 around the rotational axis 8. The signal generated by the pressure transducer 21 is also sent, through a connection 15, to a microprocessor 16. Through a further connecting element 17, an electrical signal related to the angular position of the intercepting element 3 is sent from the servomechanism 14 to the microprocessor 16. A further connecting element 30 connects the microprocessor 16 to the servomechanism 14 to control the latter, forming a closed loop as will be further explained.

In this first embodiment of the flow meter, FIGS.1 and 2, the invention operates as follows:

The duct 4 of intercepting element 3 is the turbulence chamber, into which the flow of gas enters through passageway 5 (inspiration) or 5' (expiration).

When no pressure signals are present (flow zero between inspiration and expiration) the transducer 12 acts on the servomechanism 14 in such a way that the latter maintains the tap 1 closed. The starting of expiration or inspiration causes a pressure increase in the conduit 6, with respect to conduit 6', and when such an over-pressure exceeds a given value, the corresponding electrical signal generated by transducer 12 acts on servomechanism 14 which opens the tap 1.

If the pressure transducer 12 gives a reliable response only within a very limited pressure range, it will be preferable for it to act on the servomechanism in such a way that the position of the intercepting element 3 of tap 1 keeps a constant pressure drop in conduits 6, 6', during the whole expiration phase. The angular position of the intercepting element 3, transformed into an electrical signal within the same servomechanism 14, is sent to the microprocessor 16. The latter, keeping into account the value of Δp, coming from the transducer 12, gives the legible value of flow Q. The signal processing of microprocessor 16 is in general of the type:

$$Q = f(A_1, A_2)(\Delta p)^{\frac{1}{2}} \quad (1)$$

wherein $A_1$, $A_2$ are the areas of the input and output openings of the turbulence chamber 4. In the given example, of FIGS.1 and 2, if A denotes the common value of $A_1$ and $A_2$, the formula (1) can be written in the following way:

$$Q = g(A) \cdot A \cdot (\Delta p)^{\frac{1}{2}} \quad (2)$$

wherein g(A) represents a suitable coefficient, which, for a given geometrical structure, can be held as a constant, thus simplifying the measurement. The use of the microprocessor 16, however, allows the calculation of expressions of type (1) in whole generality.

Moreover, the microprocessor 16 can act on servomechanism 14 in a wider case than referred to above, namely, in the case in which during the entire inspiration or expiration phase, the difference in pressure Δp in the conduits 6, 6' is not kept constant. The choice of the control policy of the angular displacement of intercepting element 3, as a function of Δp, depends upon the use of the conveyor flow meter, its geometry, and upon the feature of the transducer.

If, during the operation of the conveyor flow meter, a continuous collection of samples of the breathed flows has to be carried out, this can be done through duct 7. At the same time, to avoid any interference in the measurement, an equal volume of air or gas is delivered into the duct 7'.

In the embodiment shown by FIGS. 3a through 3c, the intercepting element 18 of the tap has several ways or passages, connecting, according to the angular position of the element 18, the conduit 19, at the patient's mouth, with the input conduit 20 or with the separate output conduit 21.

Two pressure transducers 22 and 23 control the pressure variation between the conduit 19 and conduits 20 and 21, respectively, and transform such variations into electrical signals, sent to a microprocessor 24 and servomechanism 25. The latter controls the angular position of intercepting element 18, whereas the microprocessor gives the flow signal Q.

In this embodiment, the conveyor flow meter operates as follows:

When there is no pressure signal, the tap remains closed, FIG. 3a. When expiration starts, there is an increase in pressure in conduit 19, with respect to conduits 20 and 21. The two pressure variations, transformed into electrical signals by transducers 22 and 23, are sent to microprocessor 24, which, acting on servomechanism 25, puts into communication the conduits 19 and 21, FIG. 3b. When the flow meter has such a configuration, it operates as the flow meter described above.

At the end of the expiration phase, the signal Δp=0 brings the intercepting element 18 back to the closed position of FIG. 3a.

When the inspiration phase begins, there is a lowering of pressure in the conduit 19 relative to conduits 20 and 21. The two pressure variations, transformed into electrical signals by the transducers 22 and 23, are sent to microprocessor 24, which acting on the servomechanism 25 puts into communication the two conduits 19 and 20, FIG. 3c.

In FIG. 3a, for simplicity, two pressure transducers 22 and 23 are illustrated. It is possible to employ only one pressure transducer 26, FIG. 4. When Δp=0 and the intercepting element 18 is closed, the transducer 26 communicates with both ducts 20 and 21 through valves 27 and 28, each of which is closed due to the action of microprocessor 24, when Δp>0 or Δp<0, respectively.

In the embodiment illustrated in FIG. 5, the tap of the flow meter is of a three-way type. In this case, the intercepting element 29 is built so that the opening connected to the patient is always open, for whichever angular position of the intercepting element.

In the embodiment of FIG. 6, the tap of the flow meter is of the piston type, particularly useful when the servomechanism acts with an axial movement.

From the foregoing, it should be apparent that the conveyor flow meter according to the invention offers a number of advantages among which the following are important:

(1) The possibility of measuring flows within a wide range of values, to answer all the requirements in the medical field. This possibility is due to the presence of the turbulence chamber and to the servo-adjustment of the area of the input and/or output openings.

(2) The practical insensitivity to dirtiness, as the turbulence is not obtained by means of laminars or obstacles of any other type, but only with simple holes.

(3) The facility of cleaning and sterilizing.

(4) The possibility, thanks to the use of a microprocessor, of using transducers of every kind of response, including the non linear ones, so far as they are reliable, and therefore the possibility of manufacturing low-cost equipment.

(5) A remarkable reduction of the dead space, with respect to the flow meters coupled to a separate conveyor, currently used, and therefore the possibility of carrying out measurement and tests in the medical field, practically without limitations.

(6) The possibility of carrying out flow measurements during rebreathing tests under the most variable conditions (stress testing, maximum forced expiration, etc.) due to the coupling in a unique device of the flow measuring and the conveying, within a wide range of values, and therefore the possibility of carrying-out from now on high-level researches and measurements in the physiological and clinical field.

(7) The possibility to perform with the same unique instrument the evaluation of the resistance of the airways with the flow interruption method.

(8) The possibility to sample the gas in the turbulence chamber even at high sampling rates without affecting the flow measurement: these gas samples may thus be analyzed by low cost industrial analyzer.

In some applications, it can be useful to compensate the pressure drop in the turbulent chamber in order to use a zero point detector as pressure transducer to minimize its dimensions. In this case an active compensation system of the pressure drop can be easily realized through a vent or an air jet inside or outside the turbulent chamber within the measuring points.

It is to be understood that the forms of the invention herewith shown and described are to be taken as preferred examples of the same, and that various changes in the shape, size and arrangements of parts may be resorted to, without departing from the spirit of the invention or scope of the subjoined claims.

I claim:

1. A turbulence conveyor flow meter particularly for monitoring human respiratory functions, comprising:
a body portion including a cavity having three openings, a first opening to be connected to a patient's mouth, a second opening forming an input to said cavity, and a third opening forming an output from said cavity for conveying the inspired and expired air to different paths; a movable intercepting element within said cavity with at least a passage way connecting said first opening to said second opening during inspiration and to said third opening during expiration, the movement of said intercepting element causing variations of the area open to the flow;

a first pressure transducer means connected between said first opening and said second opening;

a second pressure transducer means connected between said first opening and said third opening;

said first and second pressure transducer means responsive to variable pressure drops across the openings they are associated with;

a servo mechanism connected to said first and second pressure transducer means adapted to respond to variable signals therefrom for moving said intercepting element to vary the degree of registration of said passage way with said first and second or first and third openings; and a computing means connected with and receiving signals from said first and second pressure transducer means and said servo mechanism for sending signals to said servo mechanism to control the operation of said servo mechanism and to also provide an indication of flow rate.

2. A turbulence conveyor flow meter as defined in claim 1, wherein said intercepting element is a rotary element rotated by said servo mechanism and containing two passage ways which mutually exclusively connect said first opening to said second opening and said first opening to said third opening.

3. A turbulence conveyor flow meter as defined in claim 1, and said moveable intercepting element being a rotary element and said servomechanism comprising a rotational servomotor.

4. A turbulence conveyor flow meter as defined in claim 3, and the computing means comprising a microprocessor.

5. A turbulence conveyor flow meter as defined in claim 1, and the moveable intercepting element comprising a reciprocatory element.

6. A turbulence conveyor flow meter as defined in claim 1, and breath sampling passage means connected in the body portion in communicating relationship with said through passage.

7. A turbulence conveyor flow meter as defined in claim 1, and the through passage comprising a substantially straight passage.

8. A turbulence conveyor flow meter as defined in claim 1, and said through passage comprising an arcuate passage.

* * * * *